United States Patent [19]

Heimke et al.

[11] 4,185,383

[45] Jan. 29, 1980

[54] DENTAL IMPLANT HAVING A BIOCOMPATIBLE SURFACE

[75] Inventors: Günther Heimke, Weinheim; Willi Schulte, Tübingen, both of Fed. Rep. of Germany

[73] Assignee: Friedrichsfeld GmbH. Steinzeug-und Kunststoffwerke, Mannheim, Fed. Rep. of Germany

[21] Appl. No.: 792,116

[22] Filed: Apr. 29, 1977

[30] Foreign Application Priority Data

May 4, 1976 [DE] Fed. Rep. of Germany ....... 2619650

[51] Int. Cl.² .................................................. A61C 8/00
[52] U.S. Cl. ...................................... 433/173; 433/201
[58] Field of Search ...................... 32/10 A; 128/92 C

[56] References Cited

U.S. PATENT DOCUMENTS

| | | | |
|---|---|---|---|
| 3,740,769 | 6/1973 | Haboush | 128/92 C |
| 3,797,113 | 3/1974 | Brainin | 32/10 A |
| 3,950,850 | 4/1976 | Driskell et al. | 32/10 A |
| 3,952,334 | 4/1976 | Bokros et al. | 32/10 A |
| 4,050,157 | 9/1977 | Fagan, Jr. et al. | 32/10 A |

FOREIGN PATENT DOCUMENTS

1030690 6/1953 France ..................................... 32/10 A

*Primary Examiner*—Louis G. Mancene
*Assistant Examiner*—John J. Wilson
*Attorney, Agent, or Firm*—Fisher, Christen & Sabol

[57] ABSTRACT

A dental implant of biocompatable material includes a body provided with a head for supporting bridgework or an artificial tooth and having a shaft which is provided with a series of exterior peripheral surfaces of diminishing cross-section to define a series of stepped thrust resisting surfaces perpendicular to the axis of the shaft with the proximal end of the shaft being smooth.

23 Claims, 14 Drawing Figures

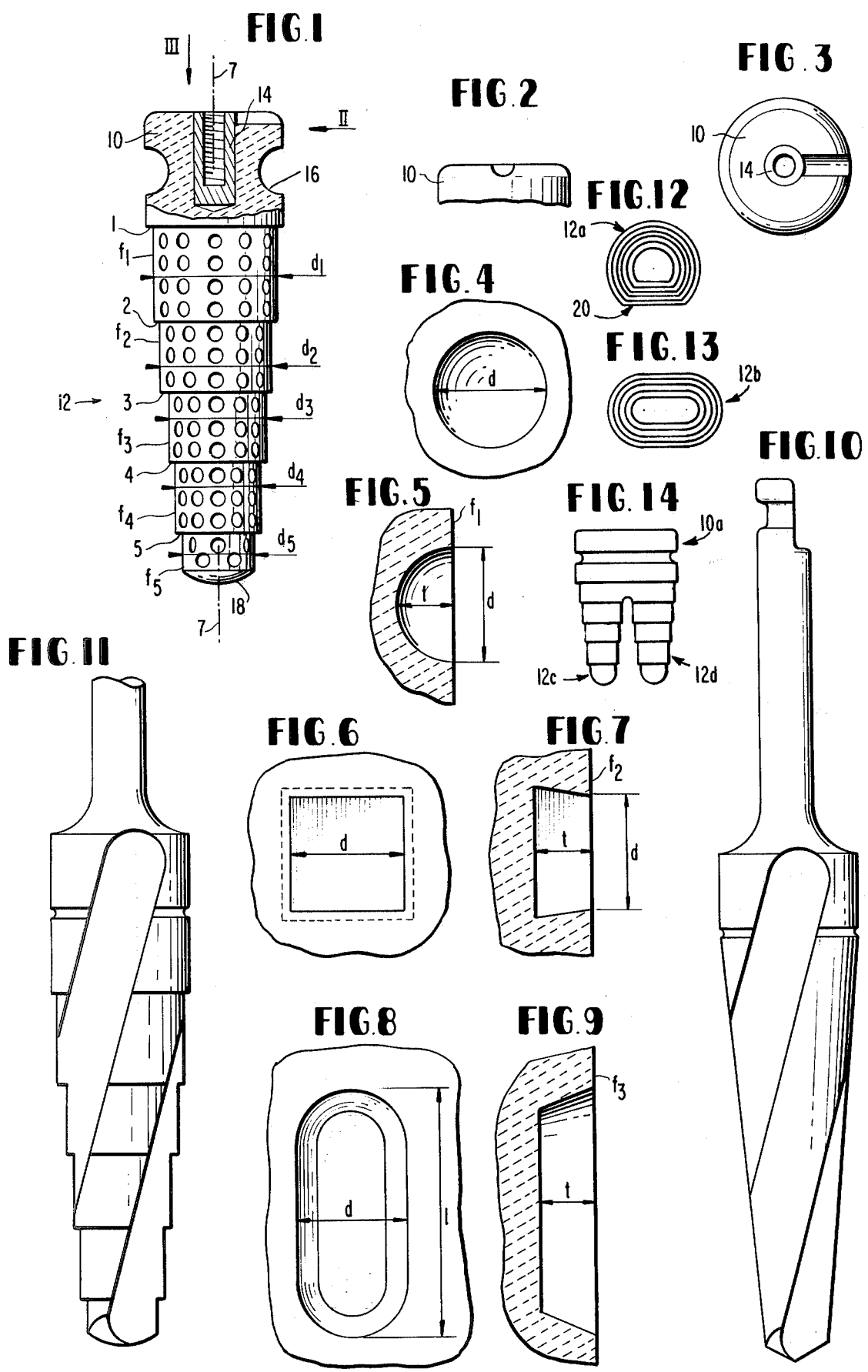

DENTAL IMPLANT HAVING A BIOCOMPATIBLE SURFACE

This invention relates to a dental implant having a biocompatible surface for the support of a dental superstructure, such as a bridge, or an artificial tooth, wherein the exposed head portion, or distal end of the implant includes anchoring means designed for the particular superstructure to be supported and wherein the shaft which supports the head is provided with a series of stepped surfaces which are perpendicular to the axis of the shaft.

In the specification and claims the word "biocompatible" is used as a definition of materials and compositions which may be either "bioinert" or "biologically benign". A material considered "bioinert" is one which exercises no influence on, and does not react with, the biological tissues, and particularly does not release any ions to the tissue within which it comes in contact. A "biologically benign" material is one which has a favorable influence on the tissue with which it comes in contact and may, to a certain extent react with it to promote the formation of bone tissue and to provide a more secure implant.

A bioinert dental implant made of an aluminum oxide ceramic has been described in "NEW ASPECTS OF IMPLANTOLOGY" by Samuel Sandhaus (pages 156–163) published by Medica. This known dental implant is provided with a shaft which resembles a threaded screw. The distal end of the implant is provided with a hexagonal head in order to enable the implant to be screwed into place by means of a wrench. The surfaces of the thread which are approximately perpendicular to the axis of the shaft are oriented toward the distal end of the implant. The proximal end is formed in the shape of a cone in order to displace the bone during the screwing in of the implant and it is provided with a slot into which the bony mass is intended to grow so as to prevent subsequent rotation and removal of the implant.

This known dental implant takes into consideration the requirement for insertion of a threaded element but does not consider the requirements which must be fulfilled in order to promote the optimal formation of bone and the preservation of the bone tissue adjacent the area of the implant.

SUMMARY OF THE INVENTION

Therefore, it is an objective of the present invention to eliminate the disadvantages of known dental implants, and one method by which this object is accomplished is to provide a threaded bushing at the distal end of the implant for the anchoring of a dental superstructure.

Another means by which the present invention constitutes an improvement is that the distal, or head, portion of the implant may be provided with an extension which can be formed, or ground, to the shape desired for attachment of a superstructure to be supported by the implant.

A further improvement in the present invention lies in the fact that the shaft that supports the heads has a cross-section which decreases in size in progressive stages towards the proximal end, these progressive decreases defining stepped surfaces lying an parallel planes which are perpendicular to the axis of the shaft and oriented towards the proximal end.

In order to preserve the bone as much as possible and to stimulate the formation of bone tissue in the jawbone in the area of the implant, the forces produced by chewing must be transmitted to the jawbone in the same direction as is the case with natural teeth and natural teeth are oriented essentially perpendicularly with respect to the curved axis of the jawbone. Since the jawbone is slightly curved in the area in which the teeth are situated, the teeth in the rear part of the jawbone do not lie in the same plane as those in the front part of the jawbone. Accordingly, the dental implants should be oriented in the same manner, but in the case of the known dental implant, this is not possible because the head of each of the implants which supports any dental superstructure is shaped in the form of a hexagon and for this reason all of the implants must be oriented precisely in parallel. In the case of the dental implant of the present invention, the anchoring structure has been developed so that it may be adapted for supporting a superstructure in such a way that the implant may be positioned in the same direction as natural teeth. In order to make this possible the implant may be provided with a threaded connection or else it may include an extension which may be shaped, or ground, to allow for positioning the supported superstructure in the position required while at the same time allowing each of the implants to also be placed in their most effective positions.

An essential assumption for exclusion of these problems, care has been taken by the use of the threaded bushing or, in the alternative, the use of a formable extension, or by some other equivalent mounting at the distal end of the implant to provide, first of all, freedom of choice in the orientation of the implant in the jawbone. By the use of the stepped surfaces and the orientation of these surfaces in relation to the proximal end of the shaft, an arrangement is achieved so that these surfaces transfer the forces produced by chewing to the tissue located below them so as to stimulate the formation of bone.

By comparison, in the case of the known dental implants, the surfaces which are approximately perpendicular with respect to the axis, must be oriented toward the distal end in order that these surfaces will be effective to drive the dental implant into the bone by the rotation of the implant. In addition, in order to prevent further rotation of the implant after it has been inserted, the proximal end is provided with a slot, or recess, into which bone mass will grow. However, this growing-in process prevents the development of tangentially oriented collagen fibers with respect to the end of the shaft. These fibers, according to three dimensional observation are capable of forming a hammock like structure which will support the dental implant resiliently.

Therefore, the proximal end of the shaft of the present invention includes no slot or recess but is rounded and provided with a smooth uninterrupted surface which permits the collagen fibers to perform their natural function. In addition, in order to prevent rotation of the implant, the surfaces of the shaft between the perpendicularly oriented steps are provided with a series of recesses extending perpendicularly into these surfaces with respect to the axis of the shaft so that bone tissue will grow into these recesses to prevent any twisting of the inserted implant.

The smooth rounded surface of the proximal end of the shaft favors the development of collagen fibers which are suspended from the interior of the bone and the formation of which is stimulated by the presence of the stepped surface adjacent the proximal end. In the case of the previously known dental implants, the anchoring in the jawbone was incomplete because of the development of soft tissue between the implant and the bone tissue. Such soft tissue has a higher metabolism rate than load-bearing bone structures. In the case of a given bacterial penetration rate inflammatory reactions did not necessarily take place in the case of traditional implants. However, in the case of this invention the possibility exists of a primarily direct bone contact without the inter-position of soft tissue especially in the area of the force transmitting surfaces. This situation calls for a low metabolism rate and therefore requires better protection against the penetration of bacteria which would endanger the growing-in process and the lasting anchoring of the implant in the bone. Therefore, in order to achieve the protection against the penetration of bacteria from the mouth cavity and in order to facilitate and improve the attachment of the epithelium on the implant, the head of the shaft is advantageously provided with an encircling constriction, or groove, and the surface of the head is highly polished in the area adjacent the groove and the area of the groove itself. The epithelium is drawn into the encircling constriction by means of a suture which encircles the constriction much in the same manner of the string which closes a tobacco pouch and the gum grows very well onto the polished surface.

In order to increase the protection against rotation of the shaft which is provied by the recesses, the cross-section of the shaft may, in addition, be non-circular. For example, at least a portion of the surface of the exterior of the shaft may be planar or, instead, the cross-section of the shaft may be elliptical in which case it is advantageous that the ratio between the length of the two axes of the ellipse should be on the order of about 1 to 3. The elliptical shape is particularly recommended whenever the implants is to be placed in the area of the molars.

The shape and depth of the recesses formed on the various exterior surfaces of the shaft may be varied. One advantageous form in which the recesses may be shaped is that of a circle, when viewing the recesses in a direction perpendicular to the axis of the shaft and the diameter of the circle (d) defined by each recess may vary between the range of between 0.15 and 1.0 mm; the depth of the recesses (f) being approximately equal to about one-half the diameter of the respective recess. In the alternative, the surface configuration of the recesses may resemble a square (as shown in FIG. 6) wherein the length of a side (d) will measure within the range between 0.15 and 1.0 mm and the depth of the square recesses (t) should be about one-half the length of one side. A third useful form of recess may consist of an outline of the surface which is oblong (as shown in FIG. 8) wherein the width of the recess (d) again measures between the range of 0.15 and 1.0 mm while the depth (t) is approximately one-half of the width.

In a situation in which teeth have been extracted from several closely adjacent alveoli it is then possible to provide an appropriate number of shafts for implantation into the empty alveoli, the several shafts, however, being connected to a single head which is provided with an encircling constriction similar to the constriction 16 previously described. The result will be that while there are three shafts the epithelium will only need to be tied in to a single head.

To increase the mechanical strength the dental implant preferably consists of a metallic core which is coated with the biocompatible material. In the present case the metallic core may comprise a high strength steel which may consist of any type of high tensile strength steel which is capable of being subjected to the necessary heat treatment required, considering that it is subject to body temperature during normal use and also to considerable amounts of alternating load variations due to normal chewing. Not only must the steel retain strength after repeated load variations but it must be capable of sustaining its strength after being subjected to heat treatment necessary for the application of the biocompatible coating. However, when the biocompatible coating is applied in accordance with one of the generally known flame spraying processes, or by some other method which subjects only the surface of the steel to heat treatment, then any change in the strength of the steel comprising the core resulting from the heat treatment will be minimal.

When a metallic core is used with a biocompatible surface coating, this coating advantageously consists of a dense non-porous ceramic or, if it is porous to any extent, the individual pores must be open only to the exterior or in communication with an adjacent pore, the criterion being that there must be complete protection against any corrosion of the metallic core which might result from body fluids. A dense coating not only protects against such contamination but has a better capability for taking a highly polished finish.

A coating having good biocompatibility comprises a ceramic material comprising at least 95%, by weight, of aluminum oxide although it is preferable that the percentage of the aluminum oxide should be as much as 99%. Impurities may upset the bicompatibility. For example titanium is often described as being biocompatible in the pertinent literature although it has turned out that when titanium is present some of the ions of the metal may react with the tissues and causes their discoloration. Furthermore, the greater the percentage of aluminum oxide in a ceramic material, the greater will be its strength.

The biocompatible surfaces need not only be bioinert but they may also be what shall be called "biologically benign," a term used to describe material such as glass ceramic, containing special ions which react favorably with animal tissue and bone. These ions control the bone reactions and stimulate the growing-on of the bone to the prosthesis. The bone formation will be improved by the formation of a transition zone between the living bone and the dead prosthesis. Such a laminar connection between the dental implant and the bone tissue will be achieved by biochemical reactions reesulting from the fact that surface components of the dental implant trigger the bone formation in the adjacent tissue and cause the development of an intermediate transition layer between the implant and the bone. Elements which are useful for the control of the tissure reactions include lithium, boron, carbon, fluorine, sodium, magnesium, silicon, phosphorous, potassium and calcium.

In a preferred form of dental implant only the stepped surfaces lying perpendicular with respect to the axis of the shaft, and the surface of the proximal end of the shaft are coated with a biologically benign composition as described above, while the surfaces connecting the stepped surfaces which lie generally parallel to the axis of the shaft are coated with bioinert composition. In this fashion the result will be that the surfaces lying parallel with the shaft eventually become connected with the surrounding bone tissue to a lesser extent when the stepped surfaces, as a result of which the dental implant is allowed to shift slightly in an axial direction with respect to the surrounding tissue after the bone tissue has become more firmly grown in with respect to the stepped surfaces.

Whenever the dental implant is fabricated with a metallic core of high strength steel, this core is to be protected by a biocompatible or biologically benign surface composition which is usually applied to the core in the form of a coating. In order for such coatings to adhere firmly to the core it is often desirable to provide an intermedite layer between the core and the applied exterior coating. Such intermediate layer may be galvanically applied as is well known, or other well known intermediate bonding layers may be used.

The implant according to the invention comes well seated in the jawbone and may be stressed after only about four months. Furthermore, by providing the head with a highly polished surface and an encircling groove, optimum engagement with the natural epithelium is achieved.

BRIEF DESCRIPTION OF THE DRAWINGS

Other objects and improvements will be evident to those skilled in the art after reading the following specification in connection with the annexed drawings, in which FIG. 1 is a view in elevation of a preferred form of dental constructed in accordance with this invention, with a portion of the head shown in section;

FIG. 2 is a fragmentary view in elevation of the head of the implant as viewed from the right-hand side in FIG. 1;

FIG. 3 is a plan view of the dental implant of FIG. 1;

FIGS. 4, 6, and 8 are external views of several forms of recesses which may be provided on the surfaces of the implant, shown on a greatly enlarged scale;

FIGS. 5, 7, and 9 are fragmentary cross-sections of the recesses shown respectively in 4, 6, and 8, and;

FIGS. 10 and 11 illustrate two forms of drills, shown in elevation, for forming the sockets in a jawbone for the implant of the present invention;

FIGS. 12 and 13 are respective views on a smaller scale from the lower end of two modified forms of the shaft cross-section, and;

FIG. 14 is another modified form of implant wherein the head is supported by two shafts.

DETAILED DESCRIPTION

The dental implant according to the present invention, is shown in FIG. 1, comprises a body provided at its distal end with a head, indicated generally by numeral 10, supported on at least one elongated shaft, indicated generally by numeral 12, which tapers inwardly in the direction of the proximal end 18. The head 10 also is provided with an anchoring mounting for a superstructure, such as a bridge or an artificial tooth, said anchoring comprising in one form a threaded bushing 14 made of an inert material such as gold or platinum cemented into a recess in the top of the head. Near the central portion of the exterior periphery of the head an inwardly directed annular groove 16 is provided and the surfaces of this groove and the adjacent surface of the head is preferably highly polished in order to facilitate the growing-on of the epithelium surrounding the head.

The shaft 12, which supports the head 10, is formed in one piece with a series of exterior peripheral surfaces of successively decreasing diameters which surfaces also define a series of stepped surfaces. In the transition from the head 12 to the topmost of the shaft 12 a first step, comprising the annular surface 1 is formed which lies in a plane perpendicular to the axis of the shaft, indicated by the dotted line 7—7. Thus, the cross-sectional dimension $d_1$ of the topmost section of the shaft is less than the cross-sectional dimension of the head itself and this topmost section of the shaft is succeeded by a second section having a smaller cross-section $d_2$ which defines the annular stepped surface 2. In this way successive exterior surfaces of the shaft having progressively decreasing diameters $d_3$, $d_4$, and $d_5$ are provided which sections define further stepped surfaces 3, 4 and 5. The proximal end 18 of the shaft is rounded in a convex form, completely smooth and without any grooves or slots or other recesses intended to reduce rotational movement so that the formation of collagen fibers will not be retarded.

The shaft 12 and the head 10 preferably consists of a dense, pore-free, highly purified aluminum oxide ceramic, the ceramic containing at least 96% by weight, and preferably as much as 99% by weight of aluminum oxide. The bone tissue and the epithelium grow onto this highly pure composition particularly favorably.

As can be seen in FIG. 3, the cross-section of the head 10 is preferably cylindrical; however, while the cross-section of the shaft 12 may, under certain circumstances, be circular, it is preferably formed with a non-circular cross-section in order to reduce any tendency of the shaft to rotate, or twist, after it has been put in place. In addition it may also be desirable to form numerous small recesses in the exterior surfaces $f_1$, $f_2$, $f_3$, $f_4$, and $f_5$ of the shaft which are interposed between the various stepped surfaces. These recesses may take a number of different forms, as illustrated on an enlarged scale in FIGS. 4–9, in which FIGS. 4 and 5 show, respectively, a plan view and cross-section of a circular concave recess, FIGS. 6 and 7 illustrate corresponding views of a square or rectangular recess, and FIGS. 8 and 9 illustrate corresponding views of an oblong recess. Incidentally, in FIGS. 6 and 7 the interior walls of the recess are undercut to increase the holding power of the recess when it has become filled with grown-in bone tissue. In connection with the oblong recess of FIGS. 8 and 9, it should be noted that it is preferable to orient the position of the oblong recess so that its longer axis lies perpendicular to the axis 7 of the shaft in order to expose as large a surface as possible perpendicular to the direction of forces exerted by chewing and thus to stimulate the bone tissue. As stated in the introduction, the width d of any of the recesses shown preferably varies within the range of between 0.15 and 1.0 mm with the depth t of the recesses measuring approximately one-half of the width d.

Implantation of a dental implant of the present invention is done directly after the extraction by insertion of the shaft 12 into the freshly opened alveolus or else the implant may be made into an artifically prepared alveolus. Implantation is particularly easy whenever the cross-section of the shaft 12 is circular because, in that case, the freshly opened alveolus may be advantageously prefilled with the conically shaped drill shown in FIG. 10 in which case the drilling need not coincide absolutely with the shape of the alveolus. After completing the drilling with the first drill the opening is completed with the drill shaped as shown in FIG. 11 whereby the respective surfaces are drilled within a precision of 0.1 mm. Preferably drilling is done by hand in order to prevent any burning of the tissue which might occur if a high speed automatic drill were to be used and also to ensure a better seating of the implant. However, where the cross-section of the shaft 12 is non-circular it is impractical to form the socket with the drills of FIGS. 10 and 11 and in that case it is preferable to use a vibrating shaping tool. One example of a non-circular shaft is shown in FIG. 12, wherein a portion of the cross-section of the shaft 12a is defined by a straight line, indicated by numeral 20; in another example, shown in FIG. 13, the shaft 12b is elliptical. Furthermore, in certain cases a single head 10a may be supported on two shafts 12c and 12d, as shown in FIG. 14.

Other modifications and improvements may be made in the invention which would fall within the scope of the following claims.

What is claimed is:

1. Dental implant comprising an elongated body provided with a surface composed of biocompatible material, the upper end of said body including a head provided with means of anchoring a superstructure to be supported by said implant, a shaft extending downwardly from the head, the exterior periphery of said shaft having stepped surfaces generally perpendicular to the axis of the shaft and of progressively decreasing mean diameter and successive peripheral surfaces of the shaft also having progressively decreasing cross-sections as the lower end of the shaft is approached, the cross-section at the upper end of each peripheral surface being at least equal to the cross-section at the lower end of the same peripheral surface, and the cross-section of each peripheral surface at its lower end being larger than the cross-section of the next lower peripheral surface, the difference between the last two mentioned cross-sections defining the adjacent stepped surface, whereby all of the stepped surfaces may lie in abutting contact with load-bearing bone tissue immediately upon implanatation.

2. Dental implant as defined in claim 1 wherein said means for anchoring a superstructure comprises a threaded bushing.

3. Dental implant as defined in claim 1 wherein said means for anchoring a superstructure comprises an extension adapted to be shaped to support a superstructure.

4. Dental implant as defined in claim 1 wherein at least one of said stepped surfaces is provided with a plurality of recesses, and the lower end of said shaft is provided with a smooth convex terminal surface.

5. Dental implant as defined in claim 4 wherein the intersections of said recesses with the exterior stepped surface are defined by circles, each having a diameter within the range of 0.15 and 1.0 mm, said recessed having depths equivalent to approximately one-half of the respective diameter.

6. Dental implant as defined in claim 4 wherein the intersections of said recesses with the exterior stepped surface are defined by squares, the length of the sides of the squares being within the range of 0.15 to 1.0 mm, said recesses having depths equivalent to approximately one-half of the length of a respective side of the square.

7. Dental implant as defined in claim 4 wherein the intersections of said recesses with the exterior stepped surfaces are oblong, the width of each recess being within the range of 0.15 to 1.0 mm, said recesses having depths equivalent to approximately one-half of the width of the respective oblong.

8. Dental implant as defined in claim 1 wherein the head of said shaft is provided with an encircling recessed surface, said recessed surface and adjacent surface of the head being highly polished.

9. Dental implant as defined in claim 1 wherein the cross-section of at least one of the stepped surfaces of the shaft is non-circular.

10. Dental implant as defined in claim 9 wherein at least a portion of said cross-section is defined by a straight line.

11. Dental implant as defined in claim 9 wherein said cross-section is elliptical.

12. Dental implant as defined in claim 11 wherein the ratio of the two axes of said elliptical cross-section is on the order of 1 to 3.

13. Dental implant as defined in claim 1 wherein said elongated body comprises a metallic core coated with a biocompatible composition.

14. Dental implant as defined in claim 13 wherein said metallic core comprises high strength steel.

15. Dental implant as defined in claim 13 wherein said elongated body includes an intermediate layer of material between said metallic core and said biocompatible composition.

16. Dental implant as defined in claim 1 wherein said biocompatible composition comprises a dense non-porous $Al_2O_3$ ceramic composition.

17. Dental implant as defined in claim 16 wherein said ceramic composition includes at least 95% by weight, of $Al_2O_3$.

18. Dental implant as defined in claim 16 wherein said ceramic composition includes at least 99% by weight, of $Al_2O_3$.

19. Dental implant as defined in claim 1 wherein only those portions of said body to be embedded in a jawbone comprise biologically benign composition.

20. Dental implant as defined in claim 19 wherein said portions to be embedded comprise the shaft provided with said stepped surfaces.

21. Dental implant as defined in claim 19 wherein said biologically benign composition comprises a glass ceramic.

22. Dental implant as defined in claim 19 wherein said biologically benign composition includes a material selected from the group consisting of lithium, boron, carbon, fluorine, sodium, magnesium, silicon, phosphorous, potassium, and calcium.

23. Dental implant as defined in claim 1 for implantation in a plurality of adjacent alveoli, comprising a single head for supporting a superstructure joined with a plurality of shafts to be received in said alveoli.

* * * * *